United States Patent
Hisano et al.

(10) Patent No.: US 8,040,500 B2
(45) Date of Patent: Oct. 18, 2011

(54) DEFECT INSPECTION METHOD AND COMPUTER-READABLE STORAGE MEDIUM

(75) Inventors: Kazuya Hisano, Koshi (JP); Hiroshi Tomita, Koshi (JP); Tadashi Nishiyama, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 447 days.

(21) Appl. No.: 12/397,587

(22) Filed: Mar. 4, 2009

(65) Prior Publication Data
US 2009/0226077 A1   Sep. 10, 2009

(30) Foreign Application Priority Data
Mar. 10, 2008 (JP) .................................. 2008-060096

(51) Int. Cl.
*G06K 9/00* (2006.01)
(52) U.S. Cl. ......................... 356/149; 382/145
(58) Field of Classification Search ........... 382/141–152
See application file for complete search history.

(56) References Cited

U.S. PATENT DOCUMENTS

| | | | |
|---|---|---|---|
| 5,684,566 A * | 11/1997 | Stanton | 355/67 |
| 6,013,911 A * | 1/2000 | Hibbard et al. | 250/205 |
| 7,200,258 B2 * | 4/2007 | Lee et al. | 382/145 |
| 7,239,389 B2 * | 7/2007 | Baer et al. | 356/369 |
| 2007/0188832 A1 | 8/2007 | Hayakawa et al. | |
| 2008/0024794 A1 * | 1/2008 | Miyazaki et al. | 356/612 |

FOREIGN PATENT DOCUMENTS
JP    2007-240519    9/2007

* cited by examiner

*Primary Examiner* — Gergory J Toatley
*Assistant Examiner* — Jarreas C. Underwood
(74) *Attorney, Agent, or Firm* — Oblon, Spivak, McClelland, Maier & Neustadt, L.L.P.

(57) ABSTRACT

The present invention includes an illuminance adjustment step of setting an optimum illuminance of the illumination; and a defect inspection step of picking up the image of the substrate illuminated with the illumination at the optimum illuminance, wherein the illuminance adjustment step has: a first step of applying illuminations at different illuminances to a plurality of measurement regions on a front surface of the substrate and picking up an image of each of the measurement regions, while moving the substrate; a second step of making a luminance of the picked up image of each of the measurement regions into a histogram to find a reference luminance where an integral value from a maximum luminance side of the histogram is a predetermined value; and a third step of calculating a correlation between each of the reference luminances and the illuminance, and setting based on the correlation an illuminance at which the reference luminance coincides with a predetermined luminance, as the optimum illuminance.

20 Claims, 11 Drawing Sheets

DEFECT INSPECTION METHOD AND COMPUTER-READABLE STORAGE MEDIUM

BACKGROUND OF THE INVENTION

1. Field of the Invention

The present invention relates to a method of picking up an image of a substrate illuminated with illumination to inspect the substrate for defects, and a computer-readable storage medium.

2. Description of the Related Art

In a photolithography processing in manufacture of a semiconductor device, for example, a resist coating treatment of applying a resist solution onto, for example, a semiconductor wafer (hereinafter, referred to as a "wafer") to form a resist film, exposure processing of exposing a predetermined pattern to light on the resist film, a developing treatment of developing the exposed resist film and so on are performed in sequence to form a predetermined resist pattern on the wafer.

The wafer for which a series of predetermined photolithography processing has been performed is subjected to a so-called macro defect inspection by an inspection apparatus, such as whether or not a predetermined resist film has been formed on the front surface of the wafer, or whether or not appropriate exposure processing has been performed, and whether or not there is a scratch, or adherence of foreign substance.

Such macro defect inspection is performed such that, for example, an image pickup device of a CCD line sensor captures an image of the wafer with illumination being applied to the wafer on a mounting table, while the mounting table on which the wafer is mounted is being moved, and the image is subjected to image processing to determine presence or absence of defects (Japanese Patent Application Laid-open No. 2007-240519).

SUMMARY OF THE INVENTION

However, if the luminance of the image of the wafer is too high or too low, defects on the wafer cannot be judged in some cases. Accordingly, to appropriately perform the defect inspection, the luminance of the image of the wafer needs to be a luminance appropriate for judgment of defects on the wafer after image processing of the image. To obtain the image with such a luminance, it is necessary to apply illumination at an optimum illuminance to the wafer.

However, when setting the optimum illuminance, generally, the operation of applying illumination and picking up an image of the wafer while moving the wafer to obtain the image is repeatedly performed at different illuminances. The images of the wafer picked up at the respective illuminances are compared to one another to check the balance of the luminance of the image, and the optimum illuminance is then set. Since it is necessary to move the wafer many times and to pick up the images when the optimum illuminance is set as described above, it has taken a long time to perform the defect inspection.

The present invention has been developed in consideration of the above point, and its object is to perform defect inspection of a substrate appropriately in a short time.

To achieve the above object, the present invention is a method of picking up an image of a substrate illuminated with illumination to inspect the substrate for defects, including: an illuminance adjustment step of setting an optimum illuminance of the illumination; and a defect inspection step of picking up the image of the substrate illuminated with the illumination at the optimum illuminance, wherein the illuminance adjustment step has: a first step of applying illuminations at different illuminances to a plurality of measurement regions on a front surface of the substrate and picking up an image of each of the measurement regions, while moving the substrate; a second step of making a luminance of the picked up image of each of the measurement regions into a histogram to find a reference luminance where an integral value from a maximum luminance side of the histogram is a predetermined value; and a third step of calculating a correlation between each of the reference luminances and the illuminance, and setting based on the correlation an illuminance at which the reference luminance coincides with a predetermined luminance, as the optimum illuminance in the defect inspection step.

The predetermined luminance means the previously set luminance, and, for example, a luminance in a predetermined range from the luminance of the image obtained by picking up an image of a reference substrate having no defect. For example, when the luminance of the image of the reference substrate is 210, the predetermined luminance is set to, for example, 210±20. Once the image of the luminance at the same level as that of the reference substrate can be obtained as described above, the reference substrate and a substrate to be inspected can be appropriately compared with each other, so that the defects on the substrate can be appropriately judged. Further, when the image of the substrate is brought to have the predetermined luminance, it is avoided that, for example, the image is too bright or too dark to make judgment of defects difficult.

Moreover, from the study of the inventors, it was found that the predetermined integral value of the histogram when obtaining the appropriate reference luminance is, for example, 3% of the integral value of the whole histogram. In other words, the reference luminance is determined to be, for example, a luminance where the integral value from the maximum luminance side of the histogram is 3% of the total integral value.

According to the present invention, since, for setting the optimum illuminance of the illumination, a plurality of measurement regions are set on the substrate, and illuminations at different illuminances are applied to the plurality of measurement regions while the substrate is being moved, to pick up the image of each of the measurement regions, the image of each of the measurement regions can be obtained by a single movement of the substrate. Accordingly, it is unnecessary to move the substrate many times as in the prior art, so that the time required for setting the optimum illuminance can be reduced and therefore the defect inspection can be performed in a short time. Further, since the reference luminances of the images of the measurement regions are found and, based on the correlation between each of the reference luminances and the illuminance, the illuminance at which the reference luminance coincides with the predetermined luminance is set as the optimum illuminance, the optimum illuminance can be automatically set after the images of the measurement regions are obtained. This eliminates the necessity to directly compare the images of the substrate picked up at respective illuminances as in the prior art, so that the defect inspection can be performed in a shorter time. Furthermore, since the image of the substrate illuminated with the illumination at the optimum illuminance is picked up to obtain the image of the substrate, the image of the substrate at the above-described predetermined luminance can be obtained, so that the defects can be appropriately judged from the image of the substrate for inspection.

The present invention according to another aspect is a computer-readable storage medium storing a program running on a computer of a control unit for controlling a defect inspection unit to cause the defect inspection unit to execute the defect inspection method.

DETAILED DESCRIPTION OF THE INVENTION

Figure 1:
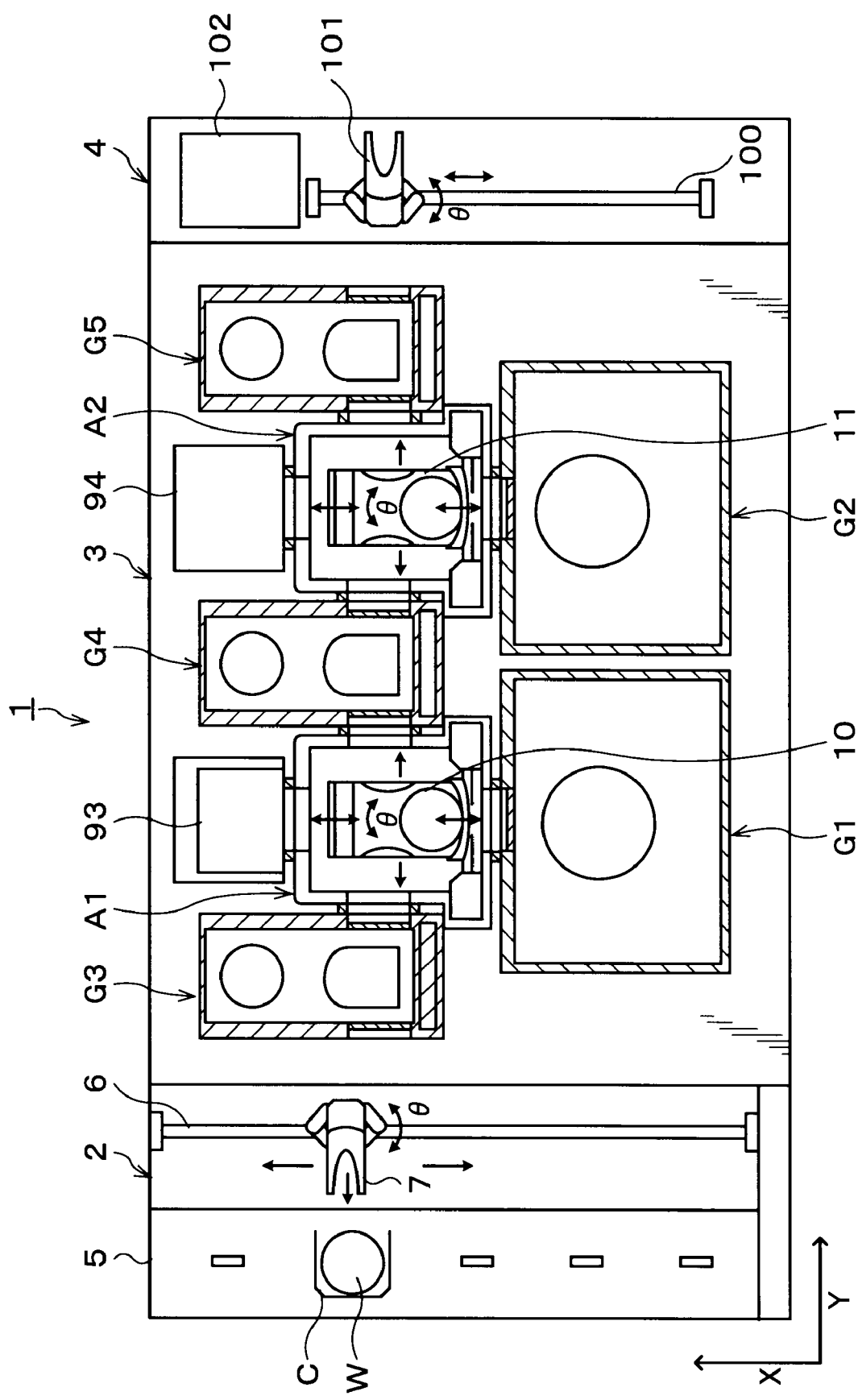
FIG. 1 is a plan view showing the outline of a configuration of a coating and developing treatment system in which a defect inspection unit for implementing a defect inspection method according to the present embodiment is incorporated.
Figure 2:
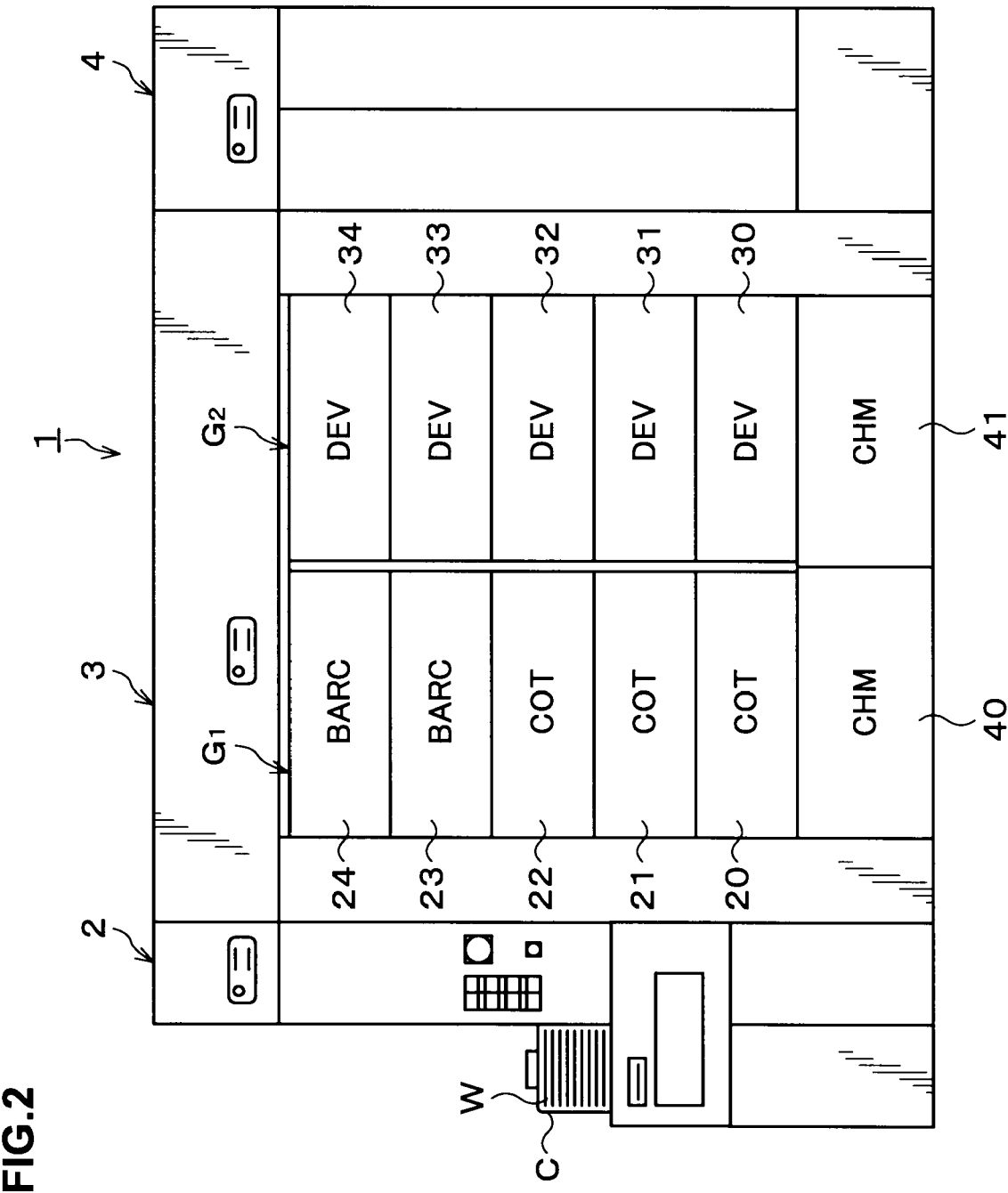
FIG. 2 is a front view of the coating and developing treatment system in FIG. 1.
Figure 3:
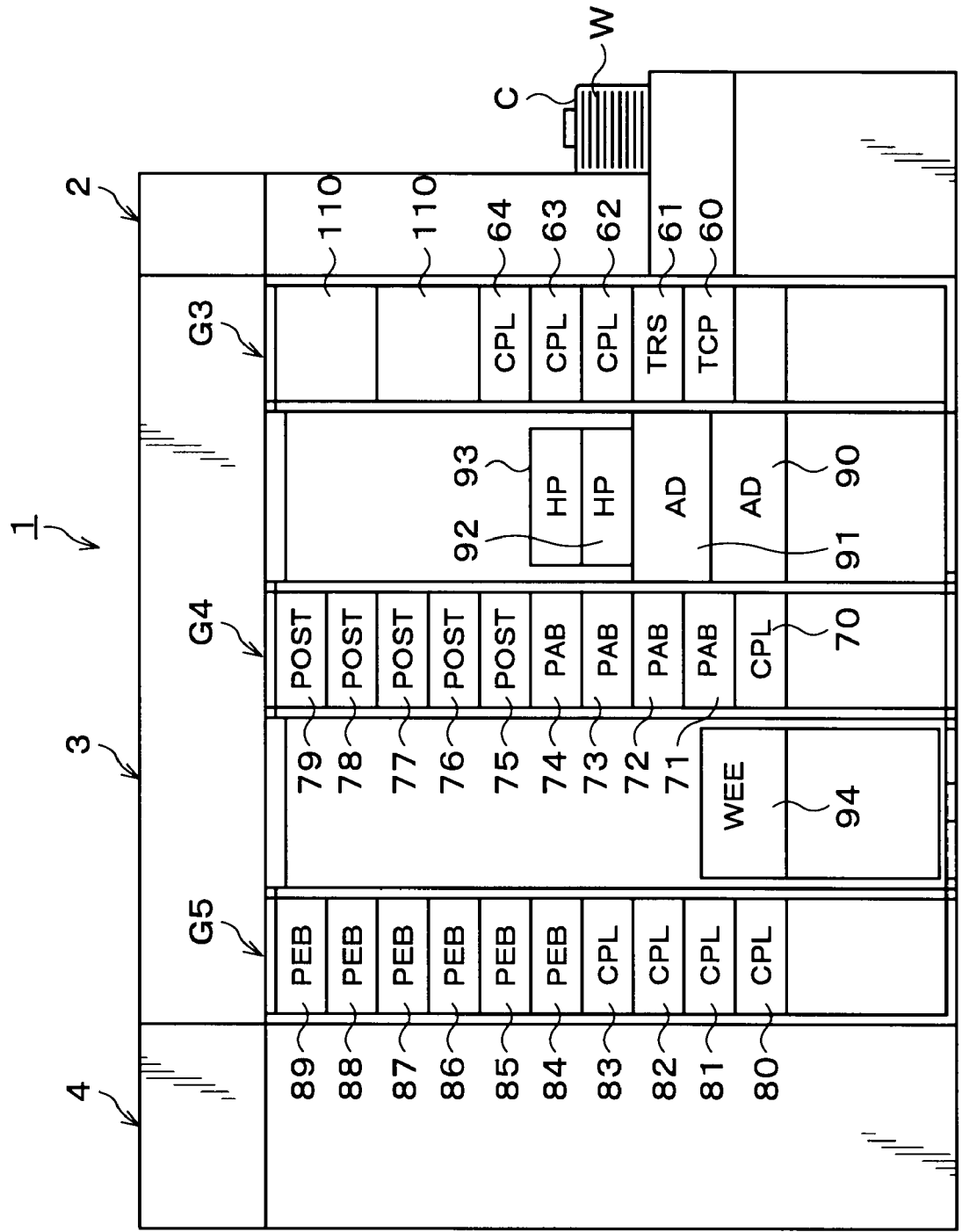
FIG. 3 is a rear view of the coating and developing treatment system in FIG. 1.

Hereinafter, preferred embodiments of the present invention will be described. FIG. 1 is a plan view showing the outline of a configuration of a coating and developing treatment system 1 in which a defect inspection unit for implementing a defect inspection method according to the present embodiment is incorporated, FIG. 2 is a front view of the coating and developing treatment system 1, and FIG. 3 is a rear view of the coating and developing treatment system 1.

The coating and developing treatment system 1 has, as shown in FIG. 1, a configuration in which, for example, a cassette station 2 for transferring, for example, 25 wafers W per cassette as a unit from/to the outside into/from the coating and developing treatment system 1 and transferring the wafers W into/out of a cassette C; a processing station 3 including a plurality of various kinds of processing and treatment units, which are multi-tiered, for performing predetermined processing or treatment in a manner of single wafer processing in a photolithography process; and an interface station 4 for passing the wafer W to/from an aligner (not shown) provided adjacent to the processing station 3, are integrally connected.

In the cassette station 2, a cassette mounting table 5 is provided and configured such that a plurality of cassettes C can be mounted on the cassette mounting table 5 in a line in an X-direction (a top-to-bottom direction in FIG. 1). In the cassette station 2, a wafer transfer body 7 is provided which is movable in the X-direction on a transfer path 6. The wafer transfer body 7 is also movable in a wafer-arrangement direction of the wafers W housed in the cassette C (a Z-direction; the vertical direction), and thus can selectively access the wafers W in each of the cassettes C arranged in the X-direction.

The wafer transfer body 7 is rotatable in a θ-direction around the Z-axis, and can access a temperature regulating unit 60 and a transition unit 61 for passing the wafer W which are included in a later-described third processing unit group G3 on the processing station 3 side.

The processing station 3 adjacent to the cassette station 2 includes, for example, five processing unit groups G1 to G5 in each of which a plurality of processing and treatment units are multi-tiered. On the side of the negative direction in the X-direction (the downward direction in FIG. 1) in the processing station 3, the first processing unit group G1 and the second processing unit group G2 are placed in order from the cassette station 2 side. On the side of the positive direction in the X-direction (the upward direction in FIG. 1) in the processing station 3, the third processing unit group G3, the fourth processing unit group G4, and the fifth processing unit group G5 are placed in order from the cassette station 2 side. Between the third processing unit group G3 and the fourth processing unit group G4, a first transfer unit A1 is provided, and a first transfer arm 10 for supporting and transferring the wafer W is provided in the first transfer unit A1. The first transfer arm 10 can selectively access the processing and treatment units in the first processing unit group G1, the third processing unit group G3, and the fourth processing unit group G4 and transfer the wafer W to them. Between the fourth processing unit group G4 and the fifth processing unit group G5, a second transfer unit A2 is provided, and a second transfer arm 11 for supporting and transferring the wafer W is provided in the second transfer unit A2. The second transfer arm 11 can selectively access the processing and treatment units in the second processing unit group G2, the fourth processing unit group G4, and the fifth processing unit group G5 and transfer the wafer W to them.

In the first processing unit group G1, as shown in FIG. 2, solution treatment units each for supplying a predetermined liquid to the wafer W to perform treatment, for example, resist coating units 20, 21, and 22 each for applying a resist solution to the wafer W, and bottom coating units 23 and 24 each for forming an anti-reflection film that prevents reflection of light at the time of exposure processing, are five-tiered in order from the bottom. In the second processing unit group G2, solution treatment units, for example, developing treatment units 30 to 34 each for supplying a developing solution to the wafer W to develop it are five-tiered in order from the bottom. Further, chemical chambers 40 and 41 each for supplying various kinds of treatment solutions to the solution treatment units in the processing unit groups G1 and G2 are provided on the lowermost tiers of the first processing unit group G1 and the second processing unit group G2, respectively.

As shown in FIG. 3, in the third processing unit group G3, the temperature regulating unit 60, the transition unit 61, high-precision temperature regulating units 62 to 64 each for temperature-regulating the wafer W under temperature control with a high precision, and defect inspection units 110 and 110 are seven-tiered in order from the bottom. Note that the configuration of the defect inspection unit 110 will be described later.

In the fourth processing unit group G4, for example, a high-precision temperature regulating unit 70, pre-baking units 71 to 74 each for performing heat processing on the wafer W after the resist coating treatment, post-baking units 75 to 79 each for heat-processing the wafer W after developing treatment, are ten-tiered in order from the bottom.

In the fifth processing unit group G5, a plurality of thermal processing units each for performing thermal processing on the wafer W, for example, high-precision temperature regulating units 80 to 83, and post-exposure baking units 84 to 89 each for heat-processing the wafer W after exposure, are ten-tiered in order from the bottom.

As shown in FIG. 1, a plurality of processing and treatment units are arranged on the positive direction side in the X-direction of the first transfer unit A1, for example, adhesion units 90 and 91 each for performing hydrophobic treatment on the wafer W and heating units 92 and 93 each for heating the wafer W being four-tiered in order from the bottom as shown in FIG. 3. As shown in FIG. 1, on the positive direction side in the X-direction of the second transfer unit A2, for example, an edge exposure unit 94 is disposed which selectively exposes only the edge portion of the wafer W to light.

In the interface station 4, for example, a wafer transfer body 101 moving on a transfer path 100 extending in the X-direction and a buffer cassette 102 are provided as shown in FIG. 1. The wafer transfer body 101 is movable in the Z-direction and also rotatable in the θ-direction and thus can access the aligner (not shown) adjacent to the interface station 4, the buffer cassette 102, and the fifth processing unit group G5 and transfer the wafer W to them.

Figure 4:
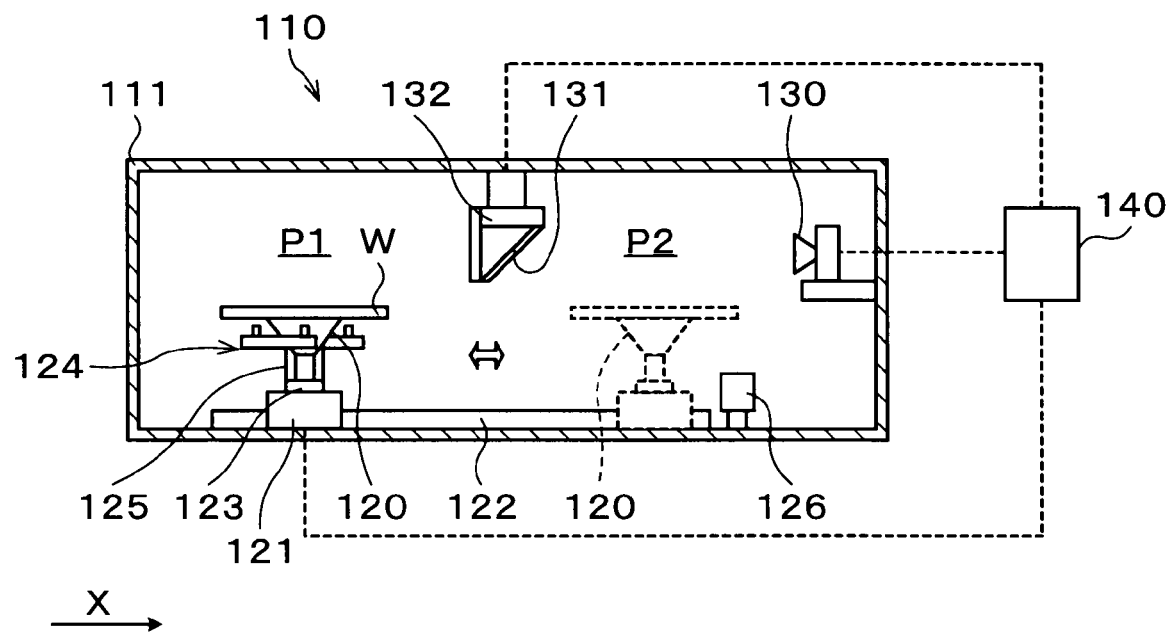
FIG. 4 is a longitudinal sectional view showing the outline of a configuration of a defect inspection unit.

Next, the configuration of the above-described defect inspection unit 110 will be described. FIG. 4 is a longitudinal sectional view showing the outline of the configuration of the defect inspection unit 110, and FIG. 5 is a transverse sectional view showing the outline of the configuration of the defect inspection unit 110.

Figure 5:
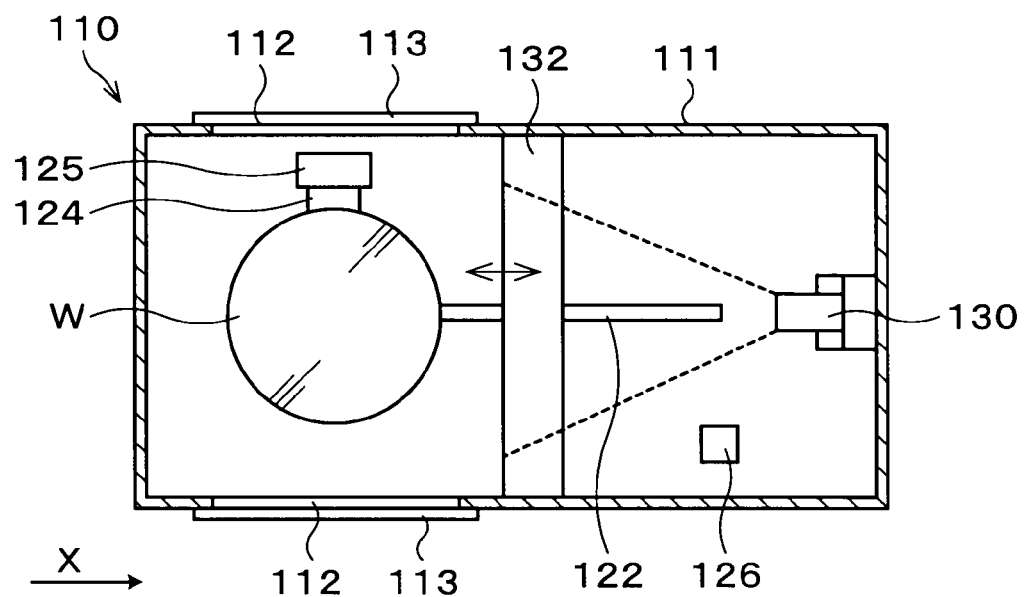
FIG. 5 is a transverse sectional view showing of the outline of the configuration of the defect inspection unit.

The defect inspection unit 110 has a casing 111 as shown in FIG. 5. Transfer-in/out ports 112 for transferring the wafer W are formed respectively in both side surfaces opposing in a short side direction of the casing 111 at one end side (on the negative direction in the X-direction in FIG. 5) of the casing 111. At the transfer-in/out ports 112, opening/closing shutters 113 are provided, respectively.

Inside the casing 111, a mounting table 120 is provided which mounts the wafer W thereon as shown in FIG. 4. This mounting table 120 freely moves and stops by means of a rotary drive unit 121 such as a motor and thus has an alignment function of adjusting the position of the wafer W. At the bottom surface of the casing 111, a guide rail 122 is provided which extends from one end side (the negative direction side in the X-direction in FIG. 4) to the other end side (the positive direction side in the X-direction in FIG. 4) in the casing 111. The mounting table 120 and the rotary drive unit 121 are provided on the guide rail 122 and can move along the guide rail 122 by means of a drive unit 123 such as a pulse motor or the like. The drive, stop, the speed of drive and so on of the drive unit 123 are controlled by a signal outputted from a control unit 140. From the drive unit 123 driven by the signal, an encoder signal at that time is outputted to the control unit 140.

Figure 6:
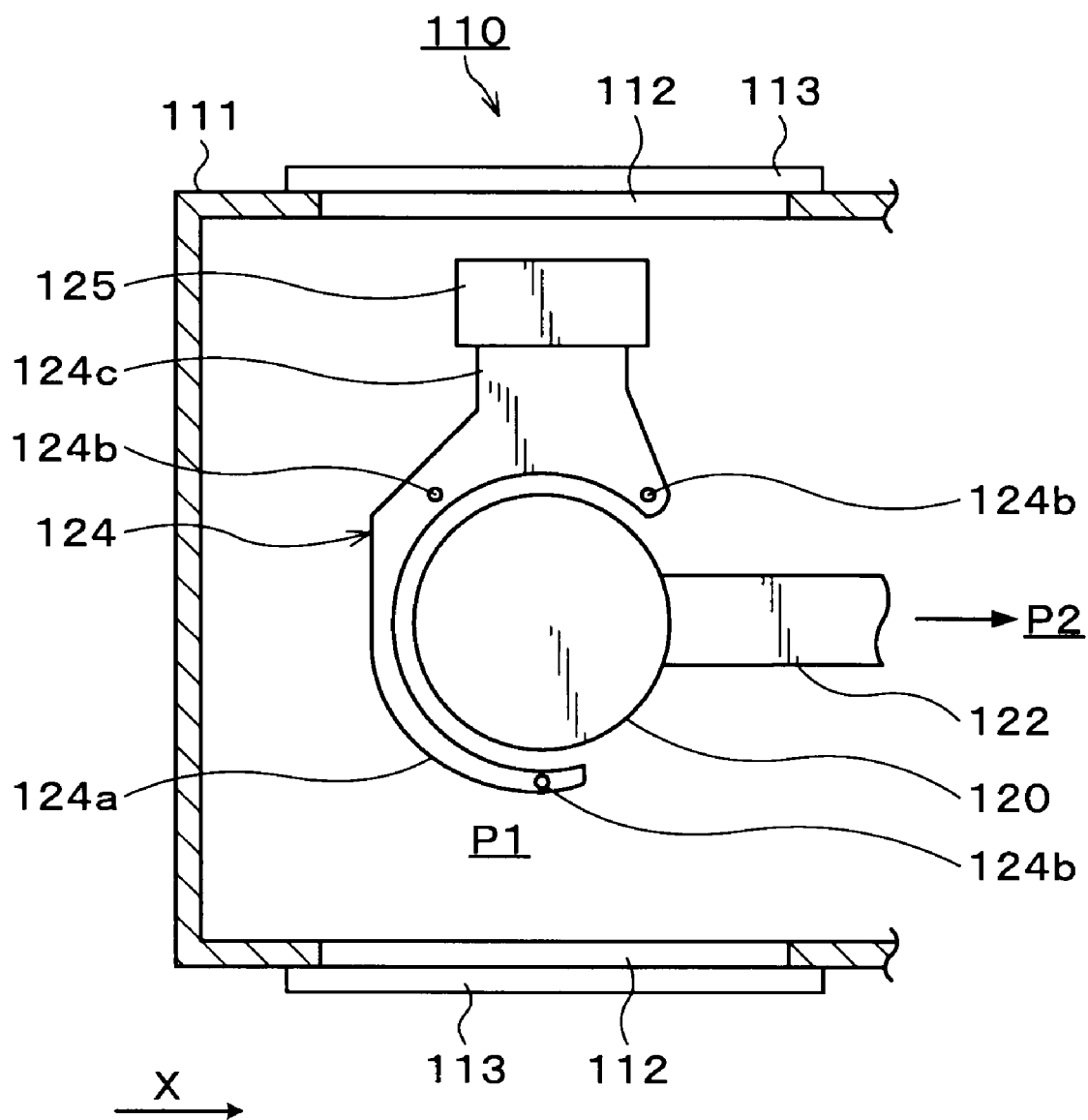
FIG. 6 is a plan view showing the outline of a configuration of a buffer arm.

A buffer arm 124 which temporarily supports the wafer W is provided on the one end side in the casing 111 and at a position P1 (a position indicated by a solid line in FIG. 4) where the wafer W is transferred into/out of the casing 111. The buffer arm 124 has a support portion 124a for the wafer W at its tip as shown in FIG. 6. The support portion 124a is formed, for example, in the shape of a ¾-circle. The diameter of the shape of a ¾-circle of the support portion 124a is larger than the diameter of the mounting table 120 and can therefore house the mounting table 120 inside the support portion 124a. A cutout portion of the shape of a ¾-circle of the support portion 124a is formed on the other end side (the side on the positive direction in the X-direction in FIG. 6) in the casing 111, so that the mounting table 120 can move to the other end side without interfering with the support portion 124a. On the support portion 124a, a plurality of support pins 124b are provided, and the wafer W is supported on the support pins 124b. A base portion 124c of the buffer arm 124 is attached to a raising and lowering drive unit 125 such as a cylinder or the like, so that the buffer arm 124 can move to positions above and below the mounting table 120.

As shown in FIG. 4, a sensor 126 which detects the position of a notch portion of the wafer W on the mounting table 120 is provided on the other end side in the casing 111 and at an alignment position P2 (a position indicated by a dotted line in FIG. 4) at which the position of the notch portion of the wafer W is adjusted. The position of the notch portion of the wafer W can be adjusted by rotating the mounting table 120 by means of the rotary drive unit 121 while the sensor 126 is detecting the position of the notch portion.

An image pickup device 130 is provided on the side surface on the other end side (the positive direction side in the X-direction in FIG. 4) in the casing 111. For the image pickup device 130, for example, a wide-angle CCD camera is used. A half mirror 131 is provided near the upper middle portion of the casing 111. The half mirror 131 is provided at a position opposite to the image pickup device 130 and inclined at 45 degrees from the vertical direction. Above the half mirror 131, an illumination device 132 whose illuminance can be changed is provided such that the half mirror 131 and the illumination device 132 are fixed to the upper surface of the casing 111. The image pickup device 130, the half mirror 131 and the illumination device 132 are separately provided above the wafer W mounted on the mounting table 120. The illumination from the illumination device 132 passes through the half mirror 131 and is applied downward. Accordingly, reflected light off an object lying within the irradiation region is reflected by the half mirror 131 and captured into the image pickup device 130. In other words, the image pickup device 130 can pick up the image of the object lying within the irradiation region.

The illumination device 132 and the image pickup device 130 are controlled by the control unit 140. The illuminance, the irradiation time and so on of the illumination of the illumination device 132 are controlled by a signal outputted from the control unit 140 to the illumination device 132. Further, image pickup, an image pickup timing, an image capture time and so on by the image pickup device 130 are controlled by a signal outputted from the control unit 140 to the image pickup device 130. The picked-up image is then outputted to the control unit 140 and subjected to necessary image processing in the control unit 140.

The above-described control unit 140 is, for example, a computer and has a program storage unit (not shown). In the program storage unit, a program is stored which controls defect inspection of the wafer W in the defect inspection unit 110. In addition, in the program storage unit, programs are also stored for controlling the operations of the above-described various processing and treatment units and the drive system such as transfer bodies to realize later-described predetermined operations in the coating and developing treatment system 1, such as application of the resist solution to the wafer W, development, heat-processing, delivery of the wafer W, control of each unit and so on. Note that the above-described programs may be ones which are recorded, for example, on a computer-readable storage medium such as a hard disk (HD), compact disk (CD), magneto-optical disk (MO), or a memory card, and installed from the storage medium into the control unit 140.

Next, the inspection for defects on the wafer W performed in the defect inspection unit 110 configured as described above will be described together with the process of wafer processing performed in the whole coating and developing treatment system 1.

First, one wafer W is taken out of the cassette C on the cassette mounting table 5 by the wafer transfer body 7 and transferred to the temperature regulating unit 60 in the third processing unit group G3. The wafer W transferred to the temperature regulating unit 60 is temperature-regulated to a predetermined temperature, and then transferred by the first transfer arm 10 to the bottom coating unit 23, where an anti-reflection film is formed. The wafer W on which the anti-reflection film has been formed is transferred by the first transfer arm 10 to the heating unit 92 and the high-precision temperature regulating unit 70 in sequence, and subjected to predetermined processing in each of the units. The wafer W is then transferred to the resist coating unit 20.

After the resist film is formed on the wafer W in the resist coating unit 20, the wafer W is transferred by the first transfer arm 10 to the pre-baking unit 71 and subsequently transferred by the second transfer arm 11 to the edge exposure unit 94 and the high-precision temperature regulating unit 83 in sequence to be subjected to predetermined processing in each of the units. The wafer W is then transferred by the wafer transfer body 101 in the interface station 4 to the aligner (not shown) where a predetermined pattern is exposed on the resist film on the wafer W. The wafer W for which the exposure processing has been completed is transferred by the wafer transfer body 101 to the post-exposure baking unit 84 and subjected to predetermined processing.

After the thermal processing in the post-exposure baking unit 84 is completed, the wafer W is transferred by the second transfer arm 11 to the high-precision temperature regulating unit 81 and temperature-regulated, and then transferred to the developing treatment unit 30 where developing treatment is performed on the wafer W, whereby a pattern is formed in the resist film. The wafer W is then transferred by the second transfer arm 11 to the post-baking unit 75 and subjected to heat-processing, and then transferred to the high-precision temperature regulating unit 63 and temperature-regulated. The wafer W is transferred by the first transfer arm 10 to the defect inspection unit 110 where the wafer W is subjected to defect inspection. Details of the defect inspection will be described later. The wafer W is then transferred by the first transfer arm 10 to the transition unit 61 and then returned by the wafer transfer body 7 to the cassette C, with which a series of photolithography process ends.

Next, the method of inspecting the wafer W for defects in the defect inspection unit 110 will be described. FIG. 7A to FIG. 7F are explanatory views showing appearances of the defect inspection unit 110 in steps of the defect inspection, and FIG. 8 shows a flowchart of the steps of the defect inspection.

Figure 7A:
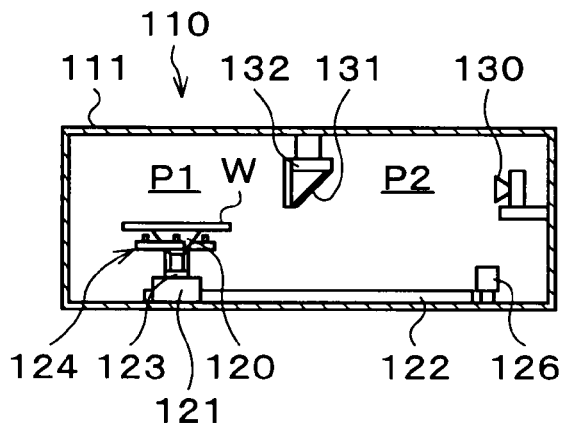
FIG. 7A to FIG. 7F are explanatory views showing appearances of the defect inspection unit in steps of defect inspection of the wafer, FIG. 7A showing a state in which the wafer is mounted on a mounting table, FIG. 7B showing a state in which the wafer on the mounting table passes under a half mirror, FIG. 7C showing a state in which the wafer on the mounting table has been moved to an alignment position, FIG. 7D showing a state in which illumination at an optimum illuminance is applied from an illumination device to the wafer, FIG. 7E showing a state in which the wafer on which the defect inspection was completed has been moved to a wafer-in/out position, and FIG. 7F showing a state in which the wafer on which the defect inspection was finished is raised by the buffer arm.
Figure 8:
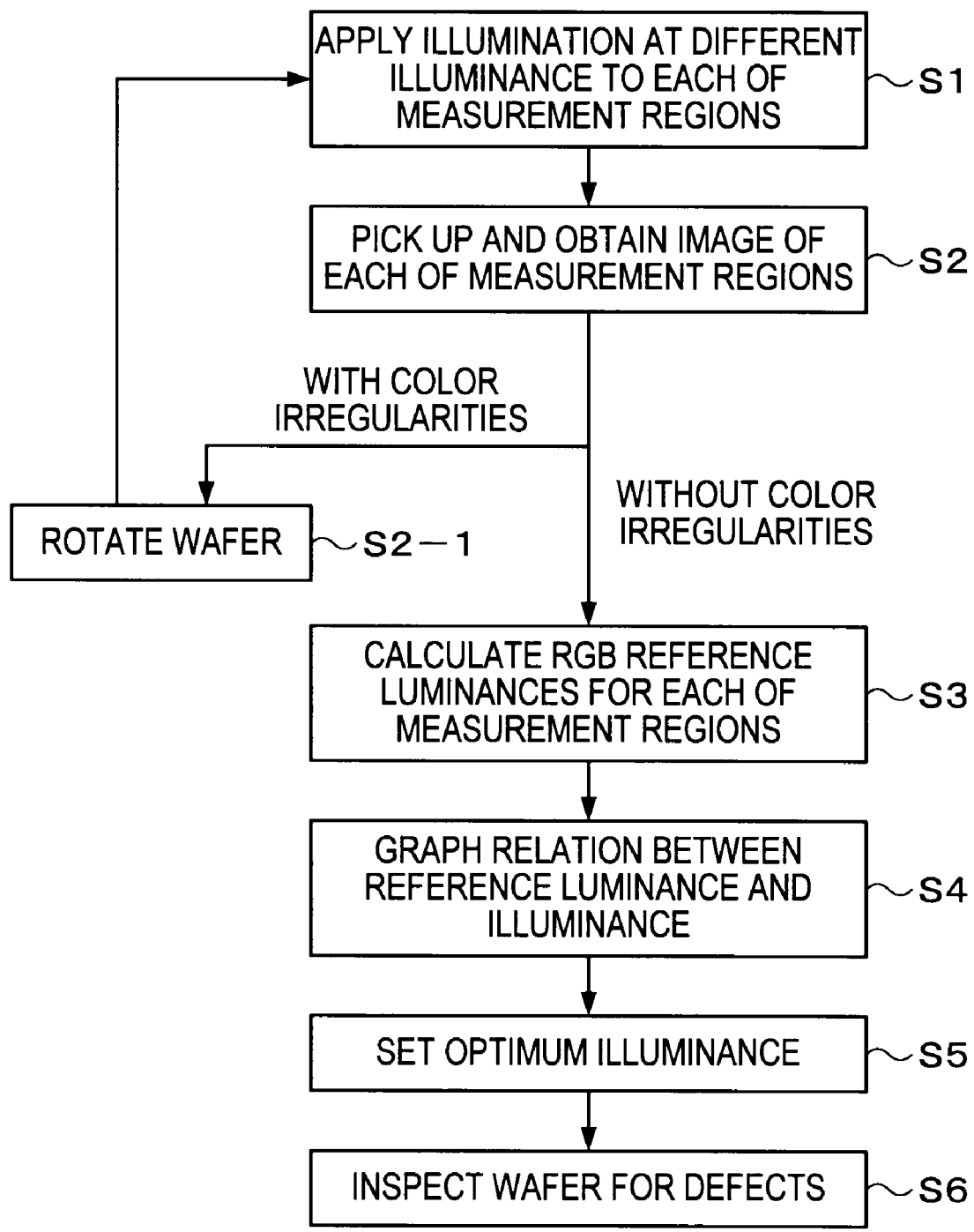
FIG. 8 is a flowchart of steps of the defect inspection of the wafer.

The wafer W transferred by the first transfer arm 10 into the casing 111 is mounted on the mounting table 120 as shown in FIG. 7A. In this event, the mounting table 120 is waiting in advance at the wafer transfer-in/out position P1 on the one end side in the casing 111.

Figure 9:
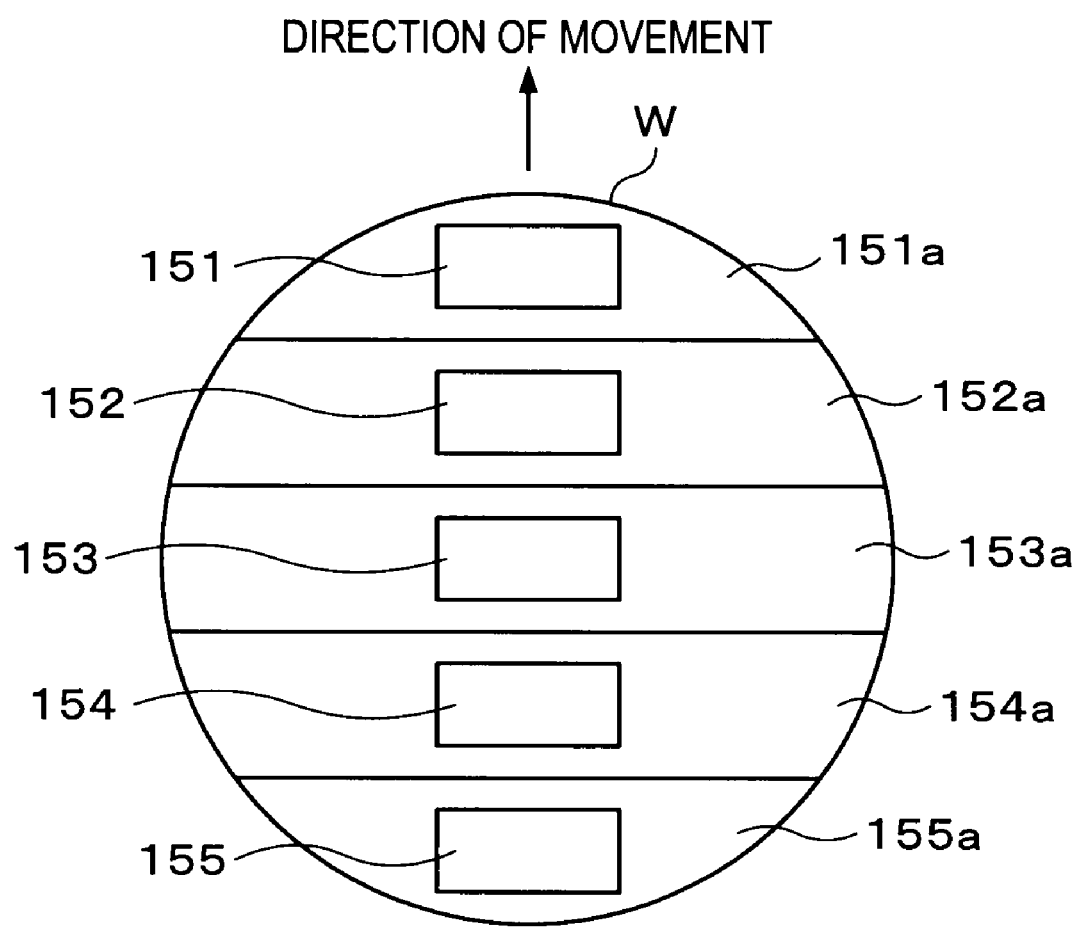
FIG. 9 is a plan view showing measurement regions on the wafer.

Here, five measurement regions 151 to 155 are set in advance on the wafer W as shown in FIG. 9 in order to subsequently set the optimum illuminance of the illumination device 132 when the defect inspection of the wafer W is performed. The measurement regions 151 to 155 are set to be arranged side by side in the direction of movement of the wafer W on the mounting table 120. Note that the reason why the number of measurement regions is set to five in this embodiment is to obtain a sufficient number of images in order to set the optimum illuminance while ensuring areas of the measurement regions, but not limited to that.

Figure 7D:
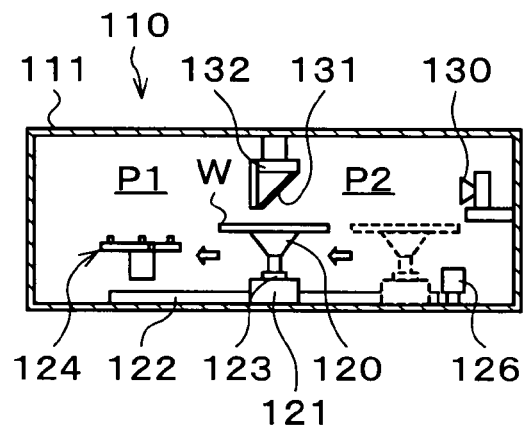
Figure 7B:
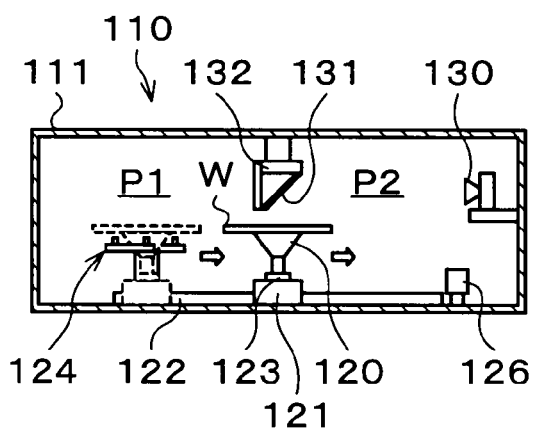

Then, illumination at a different illuminance is applied from the illumination device 132 to each of the measurement regions 151 to 155 of the wafer W when the wafer W passes under the half mirror 131 while the mounting table 120 is being moved at a predetermined speed to the alignment position P2 side as shown in FIG. 7B. In other words, the illumination to be applied to the wafer W is applied at an illuminance different for each of irradiation regions 151a to 155a including the respective measurement regions 151 to 155 shown in FIG. 9 (Step S1 in FIG. 8). In this event, the irradiation time of the illumination applied from the illumination device 132 is controlled by the control unit 140 based on the encoder signal of the drive unit 123. Note that the illuminances of the illuminations applied to the measurement regions 151 to 155 of the wafer W in this embodiment are 58, 68, 78, 88 and 98 respectively such that the applied illumination becomes brighter with the movement of the wafer W.

While the illuminations at different illuminances are applied to the measurement regions 151 to 155 of the wafer W in the above manner, the image pickup device 130 picks up images of the respective measurement regions 151 to 155 (Step S2 in FIG. 8).

The images of the measurement regions 151 to 155 picked up by the image pickup device 130 are outputted to the control unit 140. In this event, the mounting table 120 is moved by the drive unit 123 to the alignment position P2 and stopped there as shown in FIG. 7C. If color irregularities are not detected in the images of the measurement regions 151 to 155 outputted to the control unit 140, the process proceeds to a later-described Step S3. Note that the color irregularities are caused, for example, by picking up images using the wide-angle image pickup device 130 or the like.

Meanwhile, if color irregularities are detected in the images of the measurement regions 151 to 155 outputted to the control unit 140, the wafer W is rotated to a position where the color irregularities disappear in the picked-up images while the sensor 126 is detecting the position of the notch portion of the wafer W. In this embodiment, the wafer W is rotated, for example, by 90 degrees (Step S2-1 in FIG. 8). Then, the mounting table 120 is moved again to the wafer transfer-in/out position P1, the illumination at the different illuminance is then applied to each of the measurement regions 151 to 155 of the wafer W by the same method as those in the above-described Steps S1 and S2, and the image pickup device 130 picks up the image of the wafer W to obtain the images of the measurement regions 151 to 155 without color irregularities.

Once the images of the measurement regions 151 to 155 without color irregularities are outputted to the control unit 140 as described above, the control unit 140 first extracts RGB histograms of the luminance of the image of each of the measurement regions 151 to 155 to find a reference luminance for each of R (Red), G (Green) and B (Blue) (Step S3 in FIG. 8).

Figure 10:
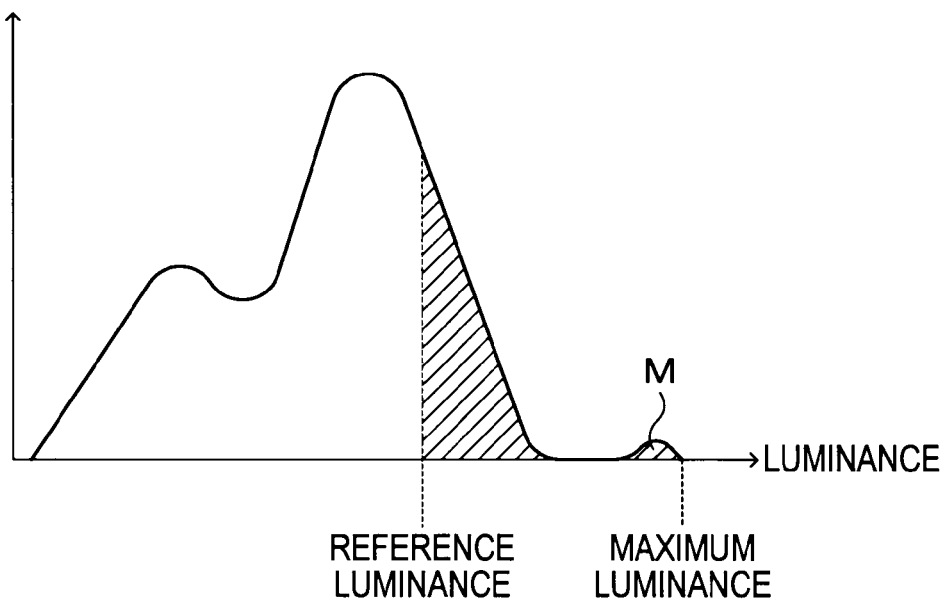
FIG. 10 is a histogram of the luminance of the image of the measurement region.

Here, a method of finding the reference luminance will be described based on FIG. 10. FIG. 10 is the histogram of the luminance for R (Red) in the image of, for example, the measurement region 151. The reference luminance is set to a luminance where the integral value from the maximum luminance side of the histogram (the hatching portion in FIG. 10) is 3% of the total integral value. This ensures that even if a bright portion M at a low frequency with respect to the entire image exists as shown in FIG. 10, the reference luminance can be appropriately found without consideration of the portion M. In such as manner, the reference luminance for each of RGB in the images of all of the measurement regions 151 to 155 is calculated.

Figure 11:
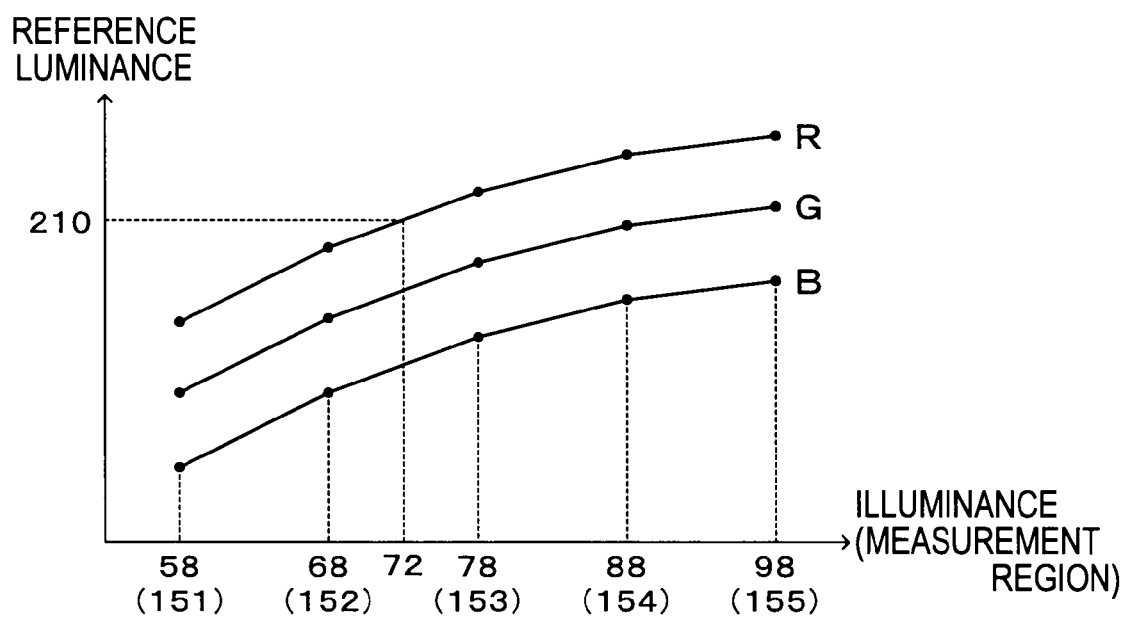
FIG. 11 is a graph showing the relation between each of the reference luminances of the RGB color system and the illuminance (measurement region)

Then, as shown in FIG. 11, a graph is created in which the reference luminances of the RGB color system are plotted for each of the measurement regions 151 to 155 (Step S4 in FIG. 8). Note that the vertical axis of the graph shown in FIG. 11 indicates the reference luminance, and the horizontal axis indicates the illuminance for each of the measurement regions 151 to 155. Further, in this graph, each of the reference luminances of the RGB color system is linearly interpolated.

Then, the illuminance at which any of the reference luminances of the RGB color system reaches a predetermined prescribed luminance is set as the optimum illuminance of the illumination device 132. More specifically, the lowest illuminance among illuminances at which any of the reference luminances of the RGB color system coincides with the predetermined luminance is set as the optimum illuminance (Step S5 in FIG. 8). The predetermined luminance is a luminance, for example, within a predetermined range from the luminance of the image obtained by picking up an image of a reference wafer having no defect. For example, when the luminance of the reference wafer is 210, the predetermined luminance is set to a range of 210±20. In this embodiment, the predetermined luminance is set to 210, and the optimum illuminance is set to 72 from the graph in FIG. 11. Note that if any of the reference luminances of the RGB color system does not reach the predetermined luminance, the optimum illuminance of the illumination device 132 is set to 150 that is the maximum illuminance.

Once the optimum illuminance of the illumination device 132 is set as described above, illumination at the optimum illuminance is applied from the illumination device 132 to the wafer W when the wafer W passes under the half mirror 131 while the mounting table 120 is being moved to the illumination device 132 side as shown in FIG. 7D. Then, the image pickup device 130 picks up the image of the front surface of the wafer W. The picked-up image is outputted to the control unit 140 and subjected to image processing in the control unit 140 so that the wafer W is inspected for defects (Step S6 in FIG. 8).

Figure 7E:
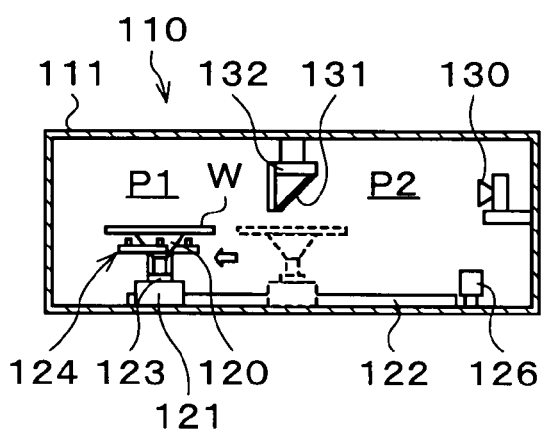
Figure 7C:
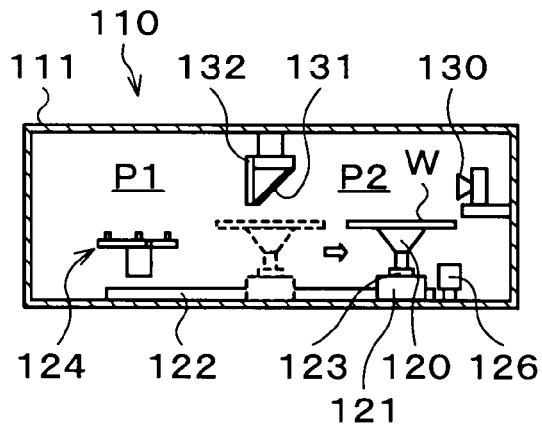
Figure 7F:
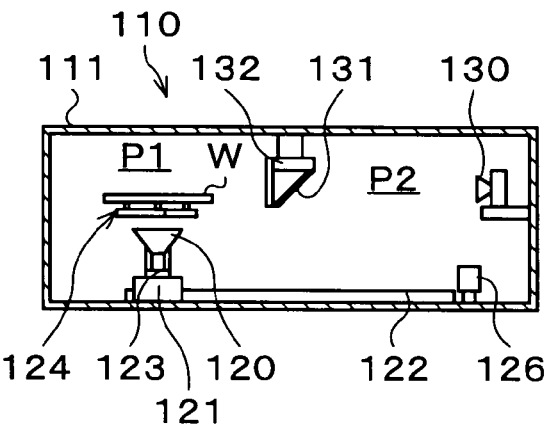

After the defect inspection of the wafer W thus ends and the mounting table 120 is moved to the wafer transfer-in/out position P1 as shown in FIG. 7E, the buffer arm 124 is raised to above the mounting table 120 as shown in FIG. 7F. This causes the buffer arm 124 to support the wafer W on the mounting table 120 and raise the wafer W from the mounting table 120. Subsequently, the wafer W is delivered from the buffer arm 124 to the wafer transfer body 7 and transferred out through the transfer-in/out port 12 by the wafer transfer body 7.

According to the above embodiment, since, for setting the optimum illuminance of the illumination device 132, a plurality of measurement regions 151 to 155 are set on the wafer W, and illumination at a different illuminance is applied from the illumination device 132 to each of the measurement regions 151 to 155 while the wafer W is being moved, to pick up the image of each of the measurement regions 151 to 155 by the image pickup device 130, the image of each of the measurement regions 151 to 155 at the different illuminance can be obtained by a single movement of the wafer W. Accordingly, it is unnecessary to move the wafer W many times as in the prior art, so that the time required for setting the optimum illuminance can be reduced and therefore the defect inspection of the wafer W can be performed in a short time.

Since the reference luminances of the RGB color system in the image of each of the measurement regions 151 to 155 are found, the reference luminances of the RGB color system are linearly interpolated to calculate the correlation between each of the reference luminances and the illuminance, and the illuminance at which the reference luminance coincides with the predetermined luminance is set as the optimum illuminance, the optimum illuminance can be automatically set after the images of the measurement regions 151 to 155 are obtained. This eliminates the necessity to directly compare the images of the wafer W picked up at respective illuminances as in the prior art, so that the defect inspection of the wafer W can be performed in a shorter time.

If color irregularities are detected in the images of the measurement regions 151 to 155 obtained at the time when the optimum illuminance is set, the wafer W is rotated to a position where the color irregularities disappear in the picked-up images, for example, by 90 degrees, and the image of the wafer W is obtained again, so that the accuracy of the image of the wafer W is higher and therefore the wafer W can be inspected for defects with a higher accuracy.

Since the image of the wafer W illuminated with the illumination at the optimum illuminance set as described above is picked up to obtain the image of the wafer W, the image of the wafer W at the predetermined luminance at substantially the same level as the luminance of the image of the reference wafer can be obtained. Thus, the image of the wafer W is brought to have an appropriate luminance, so that the wafer W can be appropriately inspected for defects based on the image of the wafer W.

Figure 12:
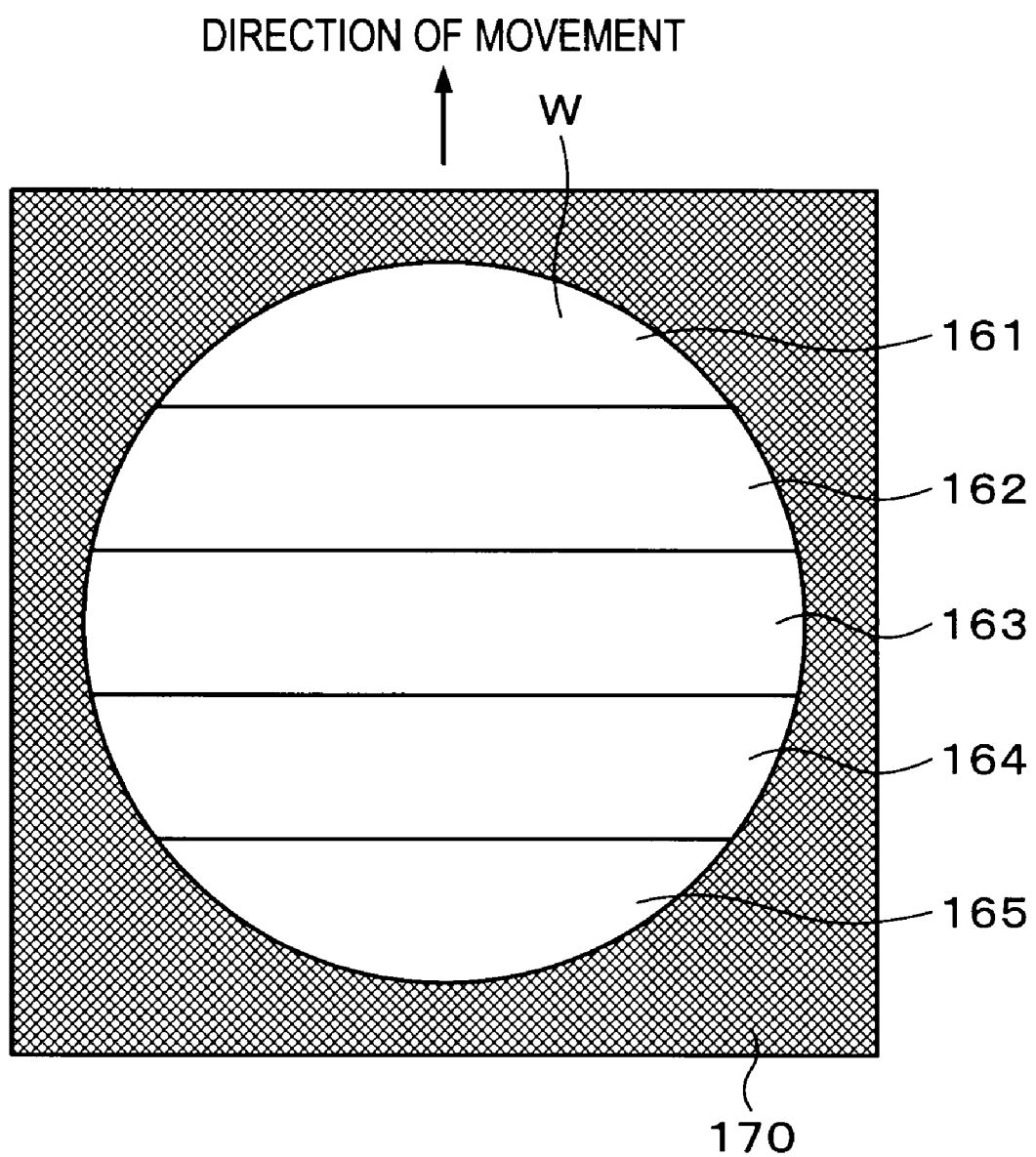
FIG. 12 is a plan view showing other measurement regions on the wafer.

Though the images of the measurement regions 151 to 155 are obtained to set the optimum illuminance of the illumination device 132 in the above embodiment, images of other measurement regions 161 to 165 which are the regions made by dividing the wafer W into a plurality of regions, that is, the irradiation regions 151a to 155a shown in FIG. 9 being regarded as the measurement regions, may be obtained as shown in FIG. 12 to set the optimum illuminance of the illumination device 132. A method of setting the optimum illuminance of the illumination device 132 in this case will be described based on a flowchart of steps shown in FIG. 13.

Figure 13:
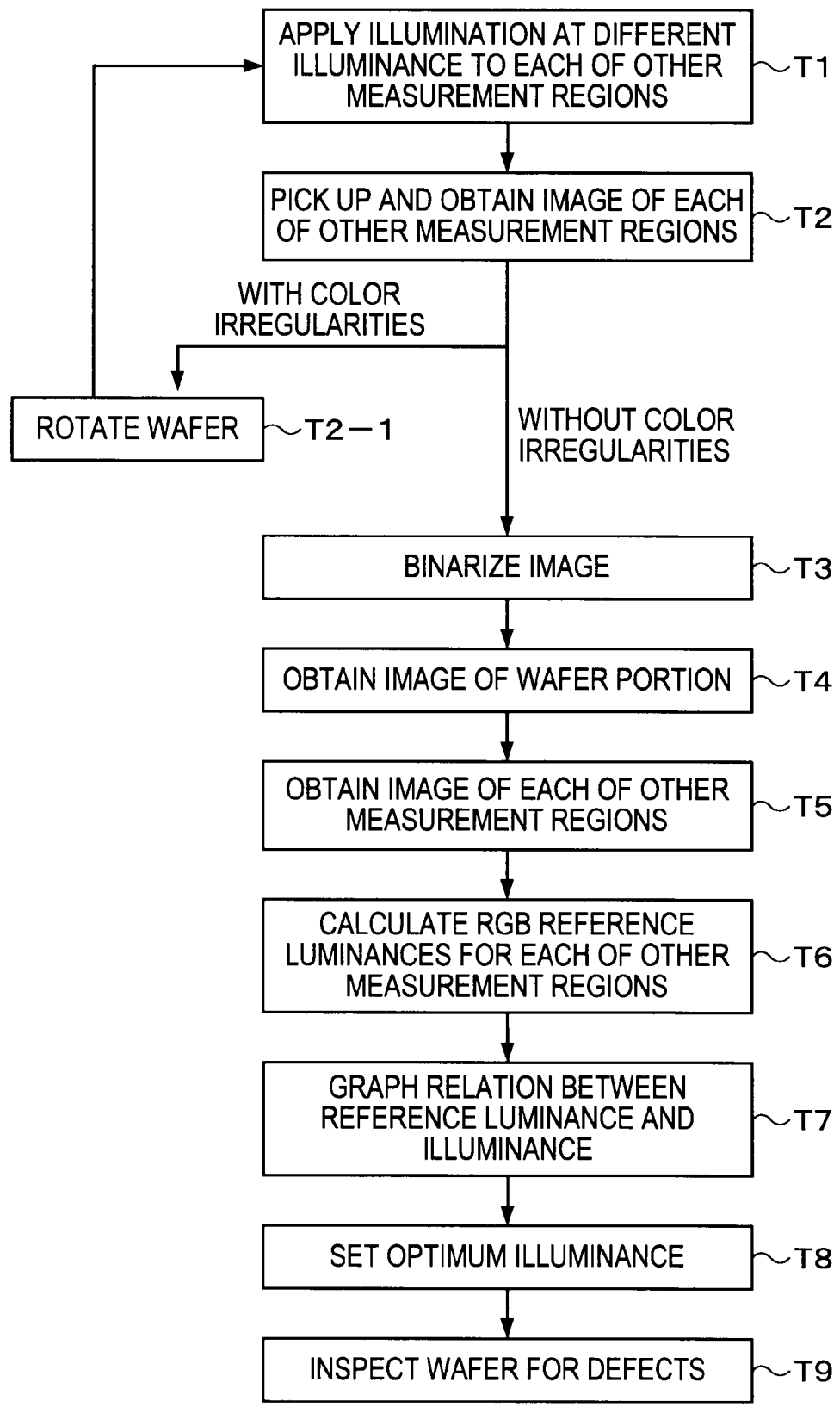
FIG. 13 is a flowchart of steps of the defect inspection of the wafer according to another embodiment.

First, illumination at a different illuminance is applied from the illumination device 132 to each of the other measurement regions 161 to 165 of the wafer W by the same method as in Step S1 in FIG. 8 (Step T1 in FIG. 13). Then, the image pickup device 130 picks up the image of the wafer W including the respective other measurement regions 161 to 165 (Step T2 in FIG. 13). In this event, the image of a region 170 outside the wafer W as shown in FIG. 12 is also picked up at the same time. Since the regions 170 is smaller in reflectivity than the wafer W, and the luminance of the image of the region 170 is smaller than the luminance of the image of the wafer W.

If color irregularities are not detected in the images outputted to the control unit 140, the process proceeds to a later-described Step T3. Meanwhile, if color irregularities are detected in the images outputted to the control unit 140, the wafer W is rotated, for example, by 90 degrees while the sensor 126 is detecting the position of the notch portion of the wafer W by the same method as in Step S2-1 in FIG. 8 (Step T2-1 in FIG. 13). Then, the mounting table 120 is moved again to the wafer transfer-in/out position P1, the illumination at the different illuminance is then applied to each of the other measurement regions 161 to 165 of the wafer W by the same method as those in the above-described Steps T1 and T2, and the image pickup device 130 picks up the image of the wafer W and the region 170 to obtain the image without color irregularities.

Once the image without color irregularities is outputted to the control unit 140 as described above, the control unit 140 first binarizes the image into the wafer W and the region 170 using the threshold value between the luminance of the image of the wafer W and the luminance of the region 170 outside the wafer W, for example, 110 (Step T3 in FIG. 13).

Next, the binarized image of the region 170 is laid, as a mask, on the image obtained by picking up the image of the wafer W and the region 170 by the image pickup device 130 so as to extract only the image of the wafer W (Step T4 in FIG. 13).

In order to divide the image of the wafer W into respective illuminances, that is, to decide boundary lines between the other measurement regions 161 to 165, gray levels in the image of the region 170 are found. Then, the boundary lines in the image of the wafer W are decided based on the boundary lines where the gray levels in the image of the region 170 are different. As a result, the image of each of the other measurement regions 161 to 165 can be obtained (Step T5 in FIG. 13). Note that when finding the gray levels in the image of the region 170, it is preferable to ignore the gray level in a peripheral portion of the region 170 in order to avoid noise.

Then, RGB histograms in the image of each of the other measurement regions 161 to 165 are extracted by the same method as those in Steps S3 to S5 in FIG. 8 to find reference luminances for the RGB color system (Step T6 in FIG. 13), and the correlation between each of the reference luminances and each of the other measurement regions 161 to 165 is graphed (Step T7 in FIG. 13). Then, the illuminance at which any of the reference luminances of the RGB color system reaches a predetermined prescribed luminance is set as the optimum illuminance of the illumination device 132 (Step T8 in FIG. 13). Subsequently, the defect inspection of the wafer W is performed using the optimum illuminance of the illumination device 132 by the same method as that in Step S6 in FIG. 8 (Step T9 in FIG. 13). Note that when the RGB histograms in the images of the other measurement regions 161 to 165 are extracted in the above-described Step T6, it is preferable not to extract the RGB histograms near the boundary lines between the other measurement regions 161 to 165 in order to avoid noise.

Also according to the above embodiment, the image of each of the other measurement regions 161 to 165 at the different illuminance can be obtained by a single movement of the wafer W, and the optimum illuminance can be automatically set based on the images of the other measurement regions 161 to 165. This makes it possible to reduce the time required for setting the optimum illuminance so that the defect inspection of the wafer W can be performed in a short time.

Since the image of the wafer W is divided into the images of the other measurement regions 161 to 165 based on the image of the region 170, and the image of the region 170 is not affected by the resist pattern formed on the wafer W, an image with higher accuracy can be obtained.

Preferred embodiments of the present invention have been described above with reference to the accompanying drawings, but the present invention is not limited to the embodiments. It should be understood that various changes and modifications are readily apparent to those skilled in the art within the scope of the spirit as set forth in claims, and those should also be covered by the technical scope of the present invention. The present invention is not limited to these embodiments but can take various forms. The present invention is also applicable to the case where the substrate is other than the wafer, such as an FPD (Flat Panel Display), a mask reticle for a photomask, and the like.

The present invention is useful in picking up an image of a substrate illuminated with illumination and inspect the substrate for defects.

What is claimed is:

1. A method of picking up an image of a substrate illuminated with illumination to inspect the substrate for defects, comprising:
    an illuminance adjustment step of setting an optimum illuminance of the illumination; and
    a defect inspection step of picking up the image of the substrate illuminated with the illumination at the optimum illuminance,
    wherein said illuminance adjustment step has:
    a first step of applying illuminations at different illuminances to a plurality of measurement regions on a front surface of the substrate and picking up an image of each of the measurement regions, while moving the substrate;
    a second step of making a luminance of the picked up image of each of the measurement regions into a histogram to find a reference luminance where an integral value from a maximum luminance side of the histogram is a predetermined value; and
    a third step of calculating a correlation between each of the reference luminances and the illuminance, and setting based on the correlation an illuminance at which the reference luminance coincides with a predetermined luminance, as the optimum illuminance in said defect inspection step.

2. The defect inspection method as set forth in claim 1, wherein in said first step, when color irregularities occur in the picked up image of each of the measurement regions, the substrate is rotated to a position where the color irregularities disappear, and an image of each of the measurement regions is picked up.

3. The defect inspection method as set forth in claim 2, wherein in said second step, reference luminances of an RGB color system of the image of each of the measurement regions are found, and
    wherein in said third step, if there are a plurality of reference luminances of the RGB color system which coincide with the predetermined luminance, an illuminance corresponding to any of the luminances of the RGB color system that is smallest among the luminances is set as the optimum illuminance in said defect inspection step.

4. The defect inspection method as set forth in claim 3,
wherein the correlation in said third step is calculated by linearly interpolating each of the reference luminances.

5. The defect inspection method as set forth in claim 3,
wherein the measurement regions are regions made by dividing the whole substrate into a plurality of portions,
wherein in said first step, illumination at a different illuminance is applied to each of the measurement regions and an image of a range including the substrate is picked up, while the substrate is being moved,
wherein the picked up image is binarized to obtain an image of a substrate portion, and
wherein the image of the substrate portion is divided into the images of the measurement regions.

6. The defect inspection method as set forth in claim 2,
wherein the correlation in said third step is calculated by linearly interpolating each of the reference luminances.

7. The defect inspection method as set forth in claim 6,
wherein the measurement regions are regions made by dividing the whole substrate into a plurality of portions,
wherein in said first step, illumination at a different illuminance is applied to each of the measurement regions and an image of a range including the substrate is picked up, while the substrate is being moved,
wherein the picked up image is binarized to obtain an image of a substrate portion, and
wherein the image of the substrate portion is divided into the images of the measurement regions.

8. The defect inspection method as set forth in claim 2,
wherein the measurement regions are regions made by dividing the whole substrate into a plurality of portions,
wherein in said first step, illumination at a different illuminance is applied to each of the measurement regions and an image of a range including the substrate is picked up, while the substrate is being moved,
wherein the picked up image is binarized to obtain an image of a substrate portion, and
wherein the image of the substrate portion is divided into the images of the measurement regions.

9. The defect inspection method as set forth in claim 8,
wherein the image of the substrate portion is divided into the images of the measurement regions based on differences in gray level in an image of a portion outside the substrate.

10. The defect inspection method as set forth in claim 1,
wherein in said second step, reference luminances of an RGB color system of the image of each of the measurement regions are found, and
wherein in said third step, if there are a plurality of reference luminances of the RGB color system which coincide with the predetermined luminance, an illuminance corresponding to any of the luminances of the RGB color system that is smallest among the luminances is set as the optimum illuminance in said defect inspection step.

11. The defect inspection method as set forth in claim 10,
wherein the correlation in said third step is calculated by linearly interpolating each of the reference luminances.

12. The defect inspection method as set forth in claim 11,
wherein the measurement regions are regions made by dividing the whole substrate into a plurality of portions,
wherein in said first step, illumination at a different illuminance is applied to each of the measurement regions and an image of a range including the substrate is picked up, while the substrate is being moved,
wherein the picked up image is binarized to obtain an image of a substrate portion, and
wherein the image of the substrate portion is divided into the images of the measurement regions.

13. The defect inspection method as set forth in claim 10,
wherein the measurement regions are regions made by dividing the whole substrate into a plurality of portions,
wherein in said first step, illumination at a different illuminance is applied to each of the measurement regions and an image of a range including the substrate is picked up, while the substrate is being moved,
wherein the picked up image is binarized to obtain an image of a substrate portion, and
wherein the image of the substrate portion is divided into the images of the measurement regions.

14. The defect inspection method as set forth in claim 13,
wherein the image of the substrate portion is divided into the images of the measurement regions based on differences in gray level in an image of a portion outside the substrate.

15. The defect inspection method as set forth in claim 1,
wherein the correlation in said third step is calculated by linearly interpolating each of the reference luminances.

16. The defect inspection method as set forth in claim 15,
wherein the measurement regions are regions made by dividing the whole substrate into a plurality of portions,
wherein in said first step, illumination at a different illuminance is applied to each of the measurement regions and an image of a range including the substrate is picked up, while the substrate is being moved,
wherein the picked up image is binarized to obtain an image of a substrate portion, and
wherein the image of the substrate portion is divided into the images of the measurement regions.

17. The defect inspection method as set forth in claim 16,
wherein the image of the substrate portion is divided into the images of the measurement regions based on differences in gray level in an image of a portion outside the substrate.

18. The defect inspection method as set forth in claim 1,
wherein the measurement regions are regions made by dividing the whole substrate into a plurality of portions,
wherein in said first step, illumination at a different illuminance is applied to each of the measurement regions and an image of a range including the substrate is picked up, while the substrate is being moved,
wherein the picked up image is binarized to obtain an image of a substrate portion, and
wherein the image of the substrate portion is divided into the images of the measurement regions.

19. The defect inspection method as set forth in claim 18,
wherein the image of the substrate portion is divided into the images of the measurement regions based on differences in gray level in an image of a portion outside the substrate.

20. A computer-readable storage medium storing a program running on a computer of a control unit for controlling a defect inspection unit to cause the defect inspection unit to execute a defect inspection method of picking up an image of a substrate illuminated with illumination to inspect the substrate for defects,
said defect inspection method, comprising:
an illuminance adjustment step of setting an optimum illuminance of the illumination; and
a defect inspection step of picking up the image of the substrate illuminated with the illumination at the optimum illuminance, wherein said illuminance adjustment step has:
a first step of applying illuminations at different illuminances to a plurality of measurement regions on a front surface of the substrate and picking up an image of each of the measurement regions, while moving the substrate;
a second step of making a luminance of the picked up image of each of the measurement regions into a histogram to find a reference luminance where an integral value from a maximum luminance side of the histogram is a predetermined value; and
a third step of calculating a correlation between each of the reference luminances and the illuminance, and setting based on the correlation an illuminance at which the reference luminance coincides with a predetermined luminance, as the optimum illuminance in said defect inspection step.

* * * * *